US012575881B2

(12) United States Patent
Govari et al.

(10) Patent No.: US 12,575,881 B2
(45) Date of Patent: Mar. 17, 2026

(54) CALIPER TOOL WITH TOGGLING BETWEEN MULTIPLE ABLATION MODES

(71) Applicant: BIOSENSE WEBSTER (ISRAEL) LTD., Yokneam (IL)

(72) Inventors: Assaf Govari, Haifa (IL); Aviva Goldberg, Hadera (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 545 days.

(21) Appl. No.: 18/088,852

(22) Filed: Dec. 27, 2022

(65) Prior Publication Data

US 2024/0206960 A1 Jun. 27, 2024

(51) Int. Cl.
| | |
|---|---|
| *A61B 18/14* | (2006.01) |
| *A61B 18/00* | (2006.01) |
| *A61B 90/00* | (2016.01) |

(52) U.S. Cl.
CPC .......... *A61B 18/1492* (2013.01); *A61B 90/37* (2016.02); *A61B 2018/00357* (2013.01); *A61B 2018/00577* (2013.01); *A61B 2018/00678* (2013.01); *A61B 2090/061* (2016.02)

(58) Field of Classification Search
CPC ................ A61B 18/1492; A61B 90/37; A61B 2090/061; A61B 2018/00357; A61B 2018/00577; A61B 2018/00678
USPC .......................................................... 606/41
See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben-Haim |
| 5,558,091 | A | 9/1996 | Acker et al. |
| 6,172,499 | B1 | 1/2001 | Ashe |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,788,967 | B2 | 9/2004 | Ben-Haim et al. |
| 6,892,091 | B1 | 5/2005 | Ben-Haim et al. |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |
| 8,456,182 | B2 | 6/2013 | Bar-Tal |
| 9,757,182 | B2 | 9/2017 | Bustan |
| 10,792,097 | B2 | 10/2020 | Ziv-Ari |
| 10,806,503 | B2 | 10/2020 | Warner |
| 2007/0185485 | A1 | 8/2007 | Hauck |
| 2015/0297151 | A1 | 10/2015 | Florent |

(Continued)

OTHER PUBLICATIONS

Vivek Y. Reddy, MD et al., Lattice-Tip Focal Ablation Catheter That Toggles Between Radiofrequency and Pulsed Field Energy to Treat Atrial Fibrillation, Circ Arrhythm Electrophysiol. 2020; 13:e008718. DOI: 10.1161/CIRCEP.120.008718, Jun. 2020, 483-495.

(Continued)

*Primary Examiner* — Beverly M Flanagan

(57) ABSTRACT

Methods and systems provide for coordinating multiple different types of ablation modes, such as Radio Frequency (RF) ablations of tissue portions with Pulsed Field ablations (PFA), for ablating tissue portions, e.g., ablation sites in the tissue, during a procedure, such as an ablation procedure on a cardiac wall.

12 Claims, 3 Drawing Sheets

(56)     References Cited

U.S. PATENT DOCUMENTS

| | | | |
|---|---|---|---|
| 2015/0342662 A1* | 12/2015 | Bustan | A61B 34/10 |
| | | | 606/34 |
| 2017/0128119 A1 | 5/2017 | Lambert | |
| 2020/0022649 A1* | 1/2020 | Rodriguez | A61B 5/4878 |
| 2020/0375555 A1* | 12/2020 | Cohen | A61B 5/339 |
| 2021/0022802 A1 | 1/2021 | Govari | |
| 2021/0298692 A1 | 9/2021 | Katz | |
| 2024/0108402 A1* | 4/2024 | Govari | A61B 18/1492 |
| 2024/0156530 A1* | 5/2024 | Zaides | A61B 34/20 |

OTHER PUBLICATIONS

European Search Report for corresponding EPA No. 23219867.1 dated Jun. 6, 2024.

* cited by examiner

CALIPER TOOL WITH TOGGLING BETWEEN MULTIPLE ABLATION MODES

TECHNICAL FIELD

The present disclosure relates generally to ablation procedures which use more than one ablation technique to ablate a designated area of tissue.

BACKGROUND

Ablation therapy is known to be applied for treating various conditions afflicting the human anatomy. One such application is in the treatment of atrial arrhythmias. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter).

There are various techniques for applying ablation therapy. Radiofrequency (RF) ablation is based on producing thermal damage to a region of tissue as consequence of focal Joule heating by the passage of alternating electric currents. One of the risks associated with RF ablation is thermal damage to surrounding tissue.

Pulsed Field Ablation (PFA) is an alternate ablation technique that consists in subjecting the tissue to brief high electric field exposures. Its mechanism of action is thought to be predominantly based on irreversible electroporation (IRE) with a significantly lower risk of thermal damage.

In some ablation procedures, a physician ablates the tissue discretely, site-by-site, using an ablation electrode to form a planned spatial trajectory of the ablation sites. In some cases, when a distance between sites along the spatial trajectory is too large, a gap in the trajectory may be formed. If gaps are present, the cardiac dysfunction may not be alleviated by the procedure. Furthermore, when a distance between sites along the spatial trajectory is too small overheating may occur.

SUMMARY

Methods and systems provide for coordinating multiple different types of ablation modes, such as Radio Frequency (RF) ablations of tissue portions with Pulsed Field ablations (PFA), for ablating tissue portions, e.g., ablation sites in the tissue, during a procedure, such as an ablation procedure on a cardiac wall.

The methods and systems operate in tissue ablation procedures, by determining a first ablation point in a tissue and an ablation mode associated with the first ablation point; determining a second ablation point in the tissue and the ablation mode associated with the second ablation point; and, selecting a threshold distance from one or more threshold distances, each of the one or more threshold distances corresponding to: 1) the ablation mode associated with the first ablation point and, 2) the ablation mode associated with the second ablation point, for example, to be ablated by an ablation catheter. It is then determined whether a distance between the first ablation point and the second ablation point is within the selected threshold distance. If the distance between the first ablation point and the second ablation is within the threshold distance, ablation may proceed, as it is within a safe range. However, If the distance between the first ablation point and the second ablation is above or below the threshold distance, ablation should not proceed, as it is potentially outside of a safe range. The system provides indications, visual and or audible, when the distance between the first and second ablation points is above and below the threshold distance.

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

Figure 1:
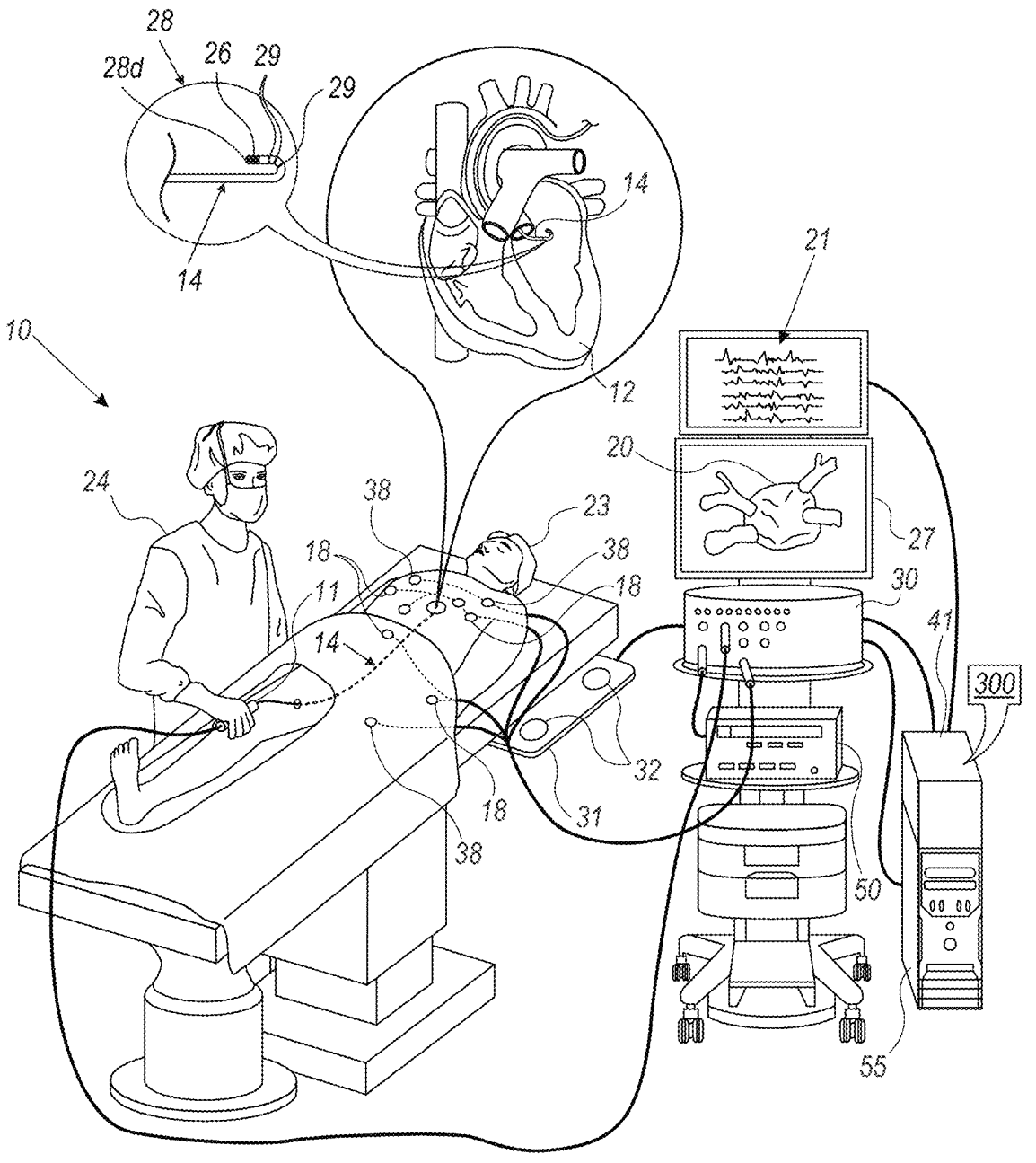
FIG. 1 is a schematic, pictorial illustration of a catheter-based ablation system, in accordance with an example of the present disclosure.

In some instances, guiding the physician to the proper distance between ablation sites and alerting the physician when deviating from the proper distance may be highly beneficial in assisting the physician in properly completing the planned spatial trajectory.

In some instances, such as ablations of the cardiac wall, a physician may wish to use more than one ablation technique to form a lesion over a selected area of tissue. For example, the physician may find it useful to ablate one or more first portions of a selected area with RF ablation and one or more second portions of the selected area with PFA.

The disclosed subject matter provides methods and systems for aiding a physician in avoiding gaps as well as unnecessary overlap when switching between two different ablation techniques, such as Radio Frequency (RF) ablations of tissue portions with Pulsed Field ablations (PFA), for ablating tissue portions, e.g., ablation sites in the tissue, during a procedure, such as an ablation procedure on a cardiac wall. Typically, when ablating along a trajectory, it is desired to maintain a recommended threshold distance. The "threshold distance", as used herein includes linear distance segments between a maximum threshold distance, and a minimum threshold distance, between ablations. The ablations used in setting the distances include a previous ablation and a projected or next ablation, based on the ablation modes of both ablations. The maximum threshold distance is the distance between ablation sites where gaps will not occur between ablations. The minimum threshold distance is a distance, within the maximum threshold distance, where overlap between ablations may occur, this overlap being unnecessary, and potentially causing overheating in one or both ablations, damaging the tissue. Optionally, even when the overlap does not lead to overheating, it may still prolong the procedure unnecessarily which is also not desired.

When ablating with PFA, the recommended threshold distance needed to avoid gaps is typically significantly shorter than that recommended for RF Ablation. Optionally, the threshold distance is defined as a range. A distance below the threshold range indicates unnecessary overlap between the previous ablation spot and the projected ablation spot, while a distance above the threshold range indicates possibility of a gap between the aforementioned ablation sites.

In some example embodiments, during an ablation procedure, each ablation site may be recorded and marked, e.g., with a virtual tag, on an EA (electro-anatomical map) of the heart chamber being treated that is displayed on a monitor. The CARTO™ 3 System, available from Biosense Webster, Inc., 31A Technology Drive, Irvine, CA 92618 is an example system that provides generating an EA map based on, for example, electrophysiological data that was previously collected with a diagnostic catheter. Typically, ablation parameters for each ablation site are recorded in association with the virtual tag displayed. Optionally, tags may be visually encoded, e.g., one color corresponding RF ablation and another color corresponding to PFA ablation. The displayed map is typically visible by the physician performing the ablation procedures, and/or the control room technician.

The disclosed system includes a caliper tool which monitors and/or determines distances between ablation points on the map, and distances between a previous ablation point (e.g., the center of the corresponding ablation spot), such as the most recent ablation point, and a projected ablation point, which is typically the next consecutive ablation point (which upon ablation becomes the next or consecutive ablation spot). The ablation points on the map correspond to the actual ablation points in the tissue, and their corresponding ablation spots, which are formed by the ablation energy extending radially outward from the ablation point during the ablating of the lesion in the tissue.

The system is designed to monitor the distance or trajectory between an ablation spot (ablation site) already made, and a position of an electrode of an ablation catheter, which will ablate a projected and next ablation spot. This distance is compared to a stored threshold distance. As a result of this comparison, the system provides indications, i.e., ablation may proceed/ablation should not proceed, which will guide the physician in placing the ablation catheter electrode, for projected or next ablation spot, within the recommended threshold distance.

Threshold distances are stored by the system. These stored threshold distances include threshold distances between the same mode of ablation, and a threshold distance between different modes of ablation. For example, there may be three different stored threshold distances: 1) a first threshold distance between two RF ablations, 2) a second threshold distance between two PFA ablations, and 3) a third threshold distance between and RF ablation and a PFA ablation. The requisite threshold distance is selected based on each ablation situation that the physician desires to perform.

Based on the ablation mode which ablated the previous ablation spot and its location, and the ablation mode for ablating the next consecutive or projected ablation spot, having a projected ablation point, along the trajectory, as identified by the system, the system automatically selects and applies the appropriate threshold distance. For example, when two ablation modes are used, such as PFA and RF ablation, the threshold distance accounts for distances of an RF ablation point being different than a PFA ablation point (i.e., PFA typically requires a higher density of ablation points than RF). When the system determines that a measured distance between the previous ablation point and the next consecutive or projected ablation point, as measured by a caliper tool on the map, will fall within (also referred to herein as exceeding) the threshold distance along the trajectory between the two ablation points ablated by their associated ablation modes, the system provides an indication of this potential occurrence. When the threshold distance is exceeded, an unwanted gap typically between the previous ablation site and the next consecutive projected ablation site typically results. When the location of the electrode that is to be used to perform the next ablation is at a distance that is less than the threshold distance overheating of the tissue may occur. The indication from the system may allow the physician to take corrective action.

The corrective action, for example, includes, readjusting the next consecutive or projected ablation point, from the previous projected ablation point (which was outside of (i.e., not within), the threshold distance or optionally, the threshold range), for example, by repositioning or moving the ablation tool, e.g., ablation catheter, and the electrode thereof. This readjustment is made to bring the distance between the previous ablation point of the existing ablation site and the new projected ablation point within the threshold distance, or optionally, inside the threshold range.

As a result of the disclosed system, an indication is provided by the system, and visual or audible to the physician, to assist the physician in ablating at the proper site in the tissue. For example, the ablations should not be too close to each other, but also, not too far, to have unwanted gaps of unablated tissue.

System Description

Reference is made to FIG. 1 showing an example catheter-based electrophysiology mapping and ablation system 10. System 10 includes multiple catheters 11, 14, which are percutaneously inserted by physician 24 through the patient's vascular system into a chamber or vascular structure of a heart 12. Typically, a delivery sheath catheter 11 is inserted into the left or right atrium near a desired location in heart 12. Thereafter, a plurality of catheters can be inserted into the delivery sheath catheter 11 to arrive at the desired location. The plurality of catheters may include catheters dedicated ablating, sensing Intracardiac Electrogram (IEGM) signals, and/or catheters dedicated for both ablating and sensing. An example catheter 14 that is configured for ablating includes a distal end 28 with an electrode 26 at the distal tip 28d of the catheter 14, which a physician 24 brings the distal end 28 of the ablation catheter to a target site, for example, a location in tissue of a cardiac wall, for ablating.

The catheter 14 may additionally include a position sensor 29 embedded in or near distal tip 28d for tracking position and orientation of the distal tip 28d, to create maps of the area being ablated. Optionally, the position sensor 29 includes a magnetic based position sensor including three magnetic coils for sensing three-dimensional (3D) position and orientation.

The magnetic based position sensor 29 may be operated together with a location pad 31 including a plurality of magnetic coils configured to generate magnetic fields in a predefined working volume. The real-time position of the distal tip 28d of the catheter 14 may be tracked based on magnetic fields generated with location pad 31 and sensed by magnetic based position sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish location reference for location pad 31 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848, 787; 7,869,865; and 8,456,182.

A recorder 41 displays electrograms 21 captured with body surface ECG electrodes 18 and intracardiac electrograms (IEGM) captured with electrodes 26 of catheter 14. Recorder 41 may include pacing capability for pacing the heart rhythm and/or may be electrically connected to a standalone pacer.

System 10 may include an ablation energy generator 50 that is adapted to conduct ablative energy to one or more of electrodes 26 at the distal tip 28d of the ablation catheter 14. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include, for example, multiple catheters, location pad 31, body surface ECG electrodes 18, electrode patches 38, ablation energy generator 50, and recorder 11. Optionally, PIU 30 additionally includes processing capability for implementing real-time computations of location of the catheters and for performing ECG calculations.

Workstation 55 includes memory, processor unit with memory or storage with appropriate operating software loaded therein, and user interface capability. The workstation 55, may include a system 300 (FIG. 3) of the disclosed subject matter, for performing the disclosed processes.

Figure 2:
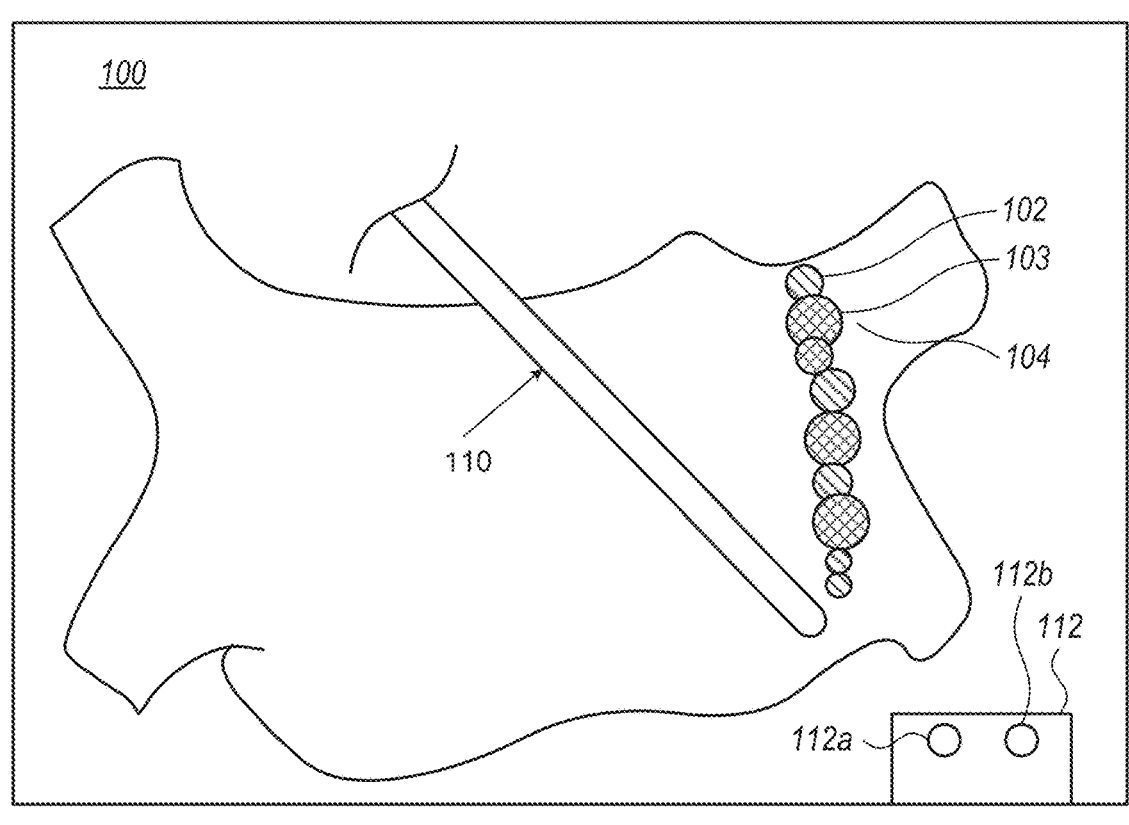
FIG. 2 is a diagram of a map showing ablation tags in accordance with the disclosed subject matter.

The workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied, such as the map 100 (FIG. 2). One commercial product embodying elements of the system 10 is available as the CARTO™3 System, detailed above.

For example, as shown in FIG. 2, a map 100 of ablation tags 102 (PFA), 103 (RF), corresponding indicate location on the tissue 104 (i.e., cardiac wall) of the actual ablations (ablation spots or ablation sites (which include the ablation point)), e.g., made by PFA 102 and RF 103 ablations. The ablation tags 102, 103, for example, are represented in different colors on the map 100, based on the mode or type of ablation, e.g., RF or PFA, which made the corresponding ablation spot. The map 100 is shown on the display 27 and is used with the ablation catheter 14, shown as a representation 110 on the map 100, for example, as part of the aforementioned CARTO™ 3 System. The representation of the ablation catheter 110 mirrors the ablation catheter 14 and its movements and locations with respect to the tissue.

In some examples, a panel 112 also appears on the map 100. The panel 112 includes indicators 112a, 112b, which are based on the location of catheter the 110 (corresponding to a projected ablation point) with respect to a previous ablation point (of a corresponding previous ablation spot). For example, the projected ablation point may be for a next consecutive ablation spot after the most recently ablated previous ablation spot, which includes its corresponding ablation point.

When the ablation catheter 14 is at a location within a threshold distance, e.g., or within a threshold range, from a previous ablation point (e.g., the most recent ablation point of the most recently ablated ablation spot), to ablate the tissue at a projected ablation point, a panel 112 does not illuminate and the physician may proceed with the ablation. When the ablation catheter 14 is at a distance above or exceeding the threshold distance, or optionally, the threshold range, a first indicator 112a, may illuminate, for example, in the color red, to signal to the physician that based on the mode (type) of the ablation to be made, i.e., RF or PFA, the ablation should not be performed. Conversely, when the ablation catheter 14 is at a distance below the threshold distance, or optionally, the threshold range, a second indicator 112b, may illuminate, for example, in the color blue, to signal to the physician that based on the mode (type) of the ablation to be made, i.e., RF or PFA, the ablation should not be performed.

For example, once the ablation catheter moves to a location within the aforementioned threshold distance, or originally, the threshold range, there is not any indicator 112a, 112b illumination indicating permission to ablate at the instant (present) catheter 14 location, corresponding to the projected ablation point. For example, as long as the ablation catheter 14 remains within a threshold distance, or optionally within a threshold range, from a previous ablation point of the previous ablation spot, based on the present ablation mode of the ablation catheter 14 and the ablation mode associated with the previous ablation point, the indicators 112a, 112b will remain unilluminated, for example, indicative of permission for the ablation catheter 14 to ablate, from the instant location of the ablation catheter 14.

Caliper Tool and Ablation Distance Tracking

Figure 3:
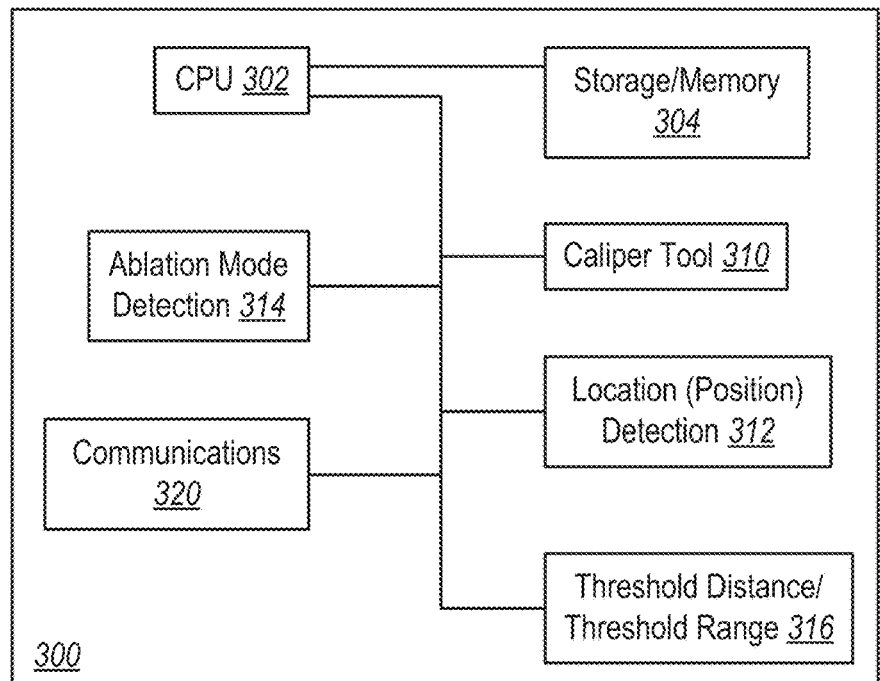
FIG. 3 is a block diagram of a system in accordance with the disclosed subject matter.

FIG. 3 shows the architecture for performing one or more processes of the disclosed subject matter. The architecture includes a system 300, which may be fully inside the workstation 55, or partially inside the workstation 55, with other components accessible over a communications network, such as the Internet, and/or the cloud. The workstation 55, for example, is of an architecture which includes one or more components for providing numerous functions and operations, and, for performing the disclosed processes. The workstation 55 may be associated with additional storage, memory, caches, and databases, both internal and external thereto.

The system 300, for example, includes a central processing unit (CPU) 302 formed of one or more processors, electronically connected, i.e., either directly or indirectly, including in electronic and/or data communication with storage/memory 304. The CPU 302 is also electronically connected, i.e., either directly or indirectly, including in electronic and/or data communication with modules for operating a caliper tool 310, catheter 14 location detection 312, ablation mode detection 314 from the ablation catheter 14, and threshold distance (calculation and analysis) 316, based on the caliper tool 310 readings coupled with the modes of the ablation catheter 14 for: 1) the projected ablation at the instant (present) location of the ablation catheter 14, and, 2) the ablation of the previous ablation spot. There is also a communications interface 320, for communicating with the PIU 30, as well as over networks such as local area networks (LANs), wide area networks (WAN), such as the Internet, and the like.

For example, a "module" includes one or components for storing instructions, (e.g., machine readable instructions) for performing one or more processes, and including or associated with processors, for example, the CPU 302, for executing the instructions.

The aforementioned components 302, 304, 310, 312, 314, 316 and 320 are in communication with each other, either directly or indirectly. While the workstation 55 is shown as a single unit, and is operable as a server or other computer, with all components 302, 304, 310, 312, 314, 316 and 320, therein, the workstation 55 may be a plurality of computers and/or servers. Additionally, one or more of the components 302, 304, 310, 312, 314, 316 and 320 may be outside of the workstation 55, including along a network or in the cloud.

The Central Processing Unit (CPU) 302 is formed of one or more processors, including microprocessors, for performing the system 300 (including workstation 55) functions and operations detailed herein, and controlling the communications interface 320. The processors are, for example, conventional processors, including hardware processors such as those used in servers, computers, and other computerized devices.

The processors of the CPU 302, for example, may comprise general-purpose computers, which are programmed in software, to carry out the functions described herein. The software may be downloaded to the computer in electronic form, over a network, for example, or it may, alternatively or additionally, be provided and/or stored on non-transitory tangible media, such as magnetic, optical, or electronic memory.

The storage/memory 304 is any conventional storage media. The storage/memory 304 stores machine executable instructions for execution by the CPU 302, to perform the disclosed processes. The processors of the CPU 302 and the storage/memory 304, although shown as a single component for representative purposes, may be multiple components, and may be outside of the workstation 55.

The caliper tool module 310, also known as the caliper tool, these terms used interchangeably herein, operates the caliper tool 310 by monitoring and/or measuring or calculating distances between the present location of the ablation catheter 14/110, as determined by the module 312, and the nearest previous ablation spot. As used herein, an ablation point is a point location on the tissue where ablation energy was delivered.

The ablation mode detection module or ablation mode detector 314 determines the present ablation mode, for example RF or PFA, to which the ablation catheter 14/110 is set.

The detected ablation modes are used by the threshold distance module 316 to analyze the determined distance, the distance between the location of the ablation catheter 14 and a previous ablation point, with respect to a threshold distance or optionally, a threshold range. The threshold distance, or optionally, the threshold range, is, for example, selected, typically automatically, by the module 316 from one or more stored threshold distances or optionally stored threshold ranges (in storage media in the module 316), based on the present ablation mode of the ablation catheter 14, and the ablation mode of the previous ablation point.

For example, should the determined distance or trajectory between ablation points be above the threshold distance, or optionally the threshold range (i.e., selected threshold distance, or optionally, the selected threshold range), the threshold distance module 316 causes the CPU 302 to signal the indicator 112*a* to illuminate (for example, in red) to indicate not to ablate (or not permitted to ablate) at the present location of the ablation catheter 14.

Conversely, for example, should the determined distance or trajectory between ablation points be below the threshold distance, or optionally, the threshold range (i.e., selected threshold distance, or optionally, the selected threshold range), the threshold distance module 316 causes the CPU 302 to signal the indicator 112*b* to illuminate (for example, in blue) to indicate not to ablate (or not permitted to ablate) at the present location of the ablation catheter 14.

The various threshold distances, or optionally threshold ranges, which are selected by the module 316, are stored in the threshold distance module 316. Example stored threshold distances, or optionally stored threshold ranges, include, for example, three different threshold distances between a previous ablation spot and the ablation mode used for the ablation, and the projected ablation point the ablation mode to be used to ablate the projected ablation point, for: 1) a threshold distance, or optionally, a threshold range, between two RF ablations (previous ablation spot and projected ablation point), 2) a threshold distance, or optionally, a threshold range, between two PFA ablations (previous ablation spot and projected ablation point), and 3) a threshold distance, or optionally, a threshold range, between an RF ablation (previous ablation spot or projected ablation point) and a PFA ablation (previous ablation spot or projected ablation point).

The ablation catheter 14, based on the ablation mode to be used to ablate the projected or next ablation point (the create a corresponding ablation spot) and the previous ablation spot and the mode used to ablate it, may be moved to locations within the requisite threshold distance or optionally threshold range, as well as locations above or below (i.e., within) the requisite threshold distance, or optionally, the threshold range. The movement of the ablation catheter 14 is monitored continuously by the system 300, so that indications to not ablate, as displayed on the respective indicators 112*a*, 112*b* on the panel 112, are made in real time and correspond to the instant actual location of the ablation catheter 14.

Additionally, the system 300 may be programmed, via the CPU 302, to deactivate the ablation catheter 14/110 when located above or below the requisite threshold distance, or optionally the threshold range, and reactivate the catheter 14/110, once the catheter 14 (and its electrode 26) location has been moved to within the requisite threshold distance, or optionally within the requisite threshold range.

Alternatively, in an optional mode, the location of the previous ablation spot, from which the determined distance or trajectory is measured is selected from any one of the plurality of locations that the physician has previously ablated. In this case the physician can select the ablation location from which the determined distance is to be measured. As a result, should the physician seek to return to an ablation spot and wants to add an additional ablation between two already made ablations, this may be done.

Figure 4:
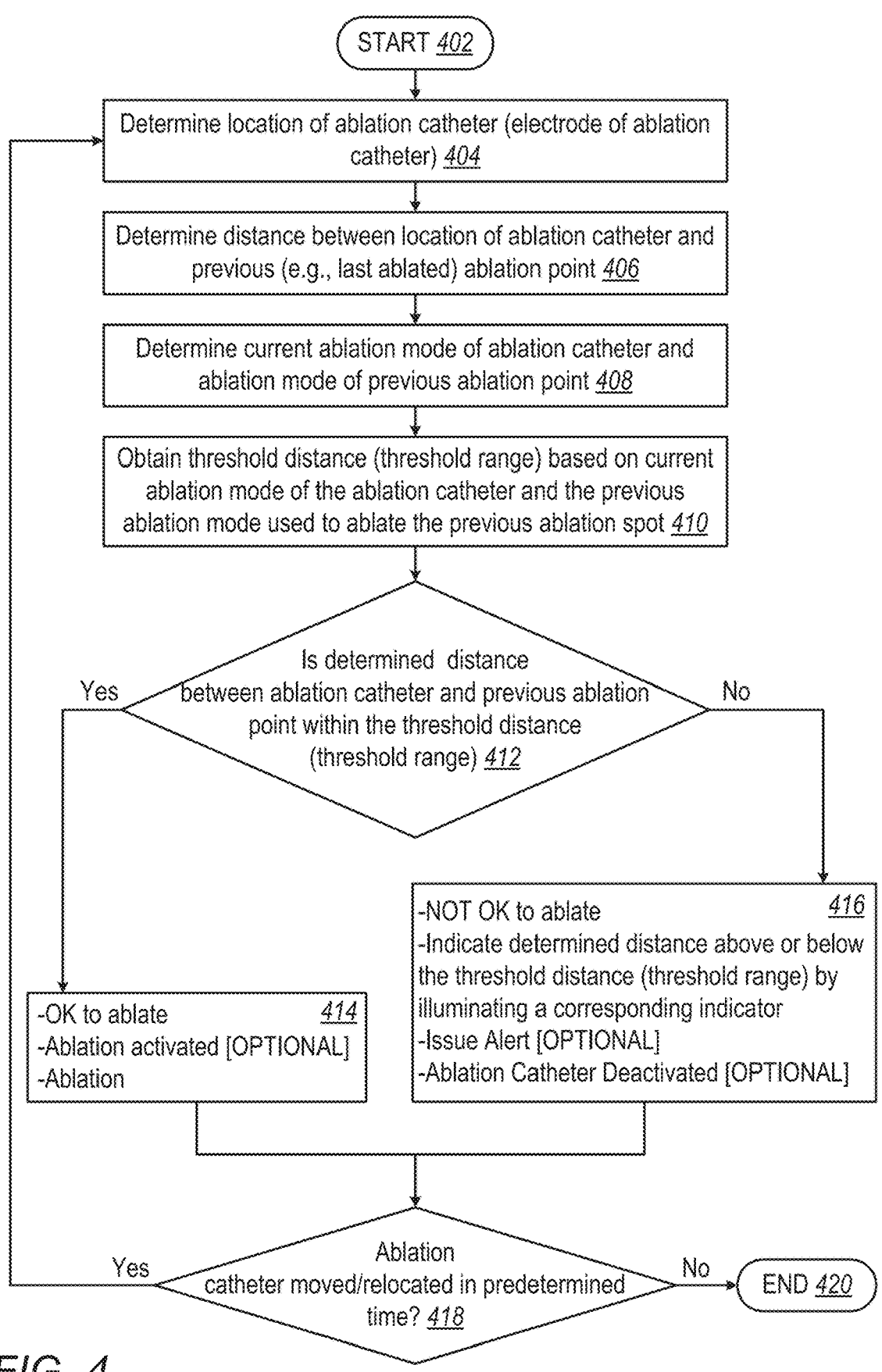
FIG. 4 is a flow diagram of an example process in accordance with the disclosed subject matter.

Attention is now directed to FIG. 4, which shows a flow diagram detailing computer-implemented processes in accordance with examples of the disclosed subject matter. Reference is also made to elements shown in FIGS. 1, 2 and 3. The process and sub-processes of FIG. 4 are computerized processes performed by the system 300. The aforementioned processes and sub-processes are, for example, performed continuously, automatically and, for example, in real time.

The process begins at a START block 402. Here, an ablation procedure is ready to be performed, for example, using an ablation catheter 14 which operates with, and is capable of moving or toggling between, multiple ablation modes, such as RF and PFA ablation modes. There is also an activated caliper tool 310, and, a mapping system, for creating a map with ablation tags corresponding to ablation spots made by RF and PFA, as shown in different colors. The mapped ablation tags 102 (PFA), 103 (RF) are representative in size and location on the tissue, to the respective corresponding actual ablation spots in the tissue. Also, all previous ablation spots, represented by ablation tags 102, 103 on the map 100, are of a known ablation mode and include a location of an ablation point (for each previous ablation spot), for example, RF (tag 103) or PFA (tag 102), are stored in storage, such as databases (not shown) in the system 300.

The process moves to block 404, where the location of the ablation catheter 14 (e.g., ablation catheter electrode 26) is determined with respect to the map 100 and the tissue 104. This location determination is made, for example, by the location detection module 312.

At block 406, the caliper tool 310 determines the distance (e.g., linear distance), known as a "determined distance" or trajectory, between the instant location of the electrode 26 of the ablation catheter 14, e.g., corresponding to the location of a projected ablation point to be made in the tissue 104, and a previous ablation point, for example, of the most recently ablated ablation spot.

The process moves to block 408, where the current ablation mode is determined for the ablation catheter (for the projected or next ablation point), and for the ablation mode of the previous ablation point (of the previous ablation spot). Based on the information received from blocks 406 and 408, the process moves to block 410.

At block 410, the threshold distance module 316 selects, for example, automatically, a threshold distance or optionally, a threshold range, based on the two ablation modes for the two ablations, previous and next or projected. The selected threshold distance or optionally, threshold range, is typically stored in the system in module 316.

The process moves to block 412, where the CPU 302 determines whether the distance between the location of the ablation catheter (e.g., its projected ablation point) and the previous ablation point, i.e., the "determined distance" or trajectory, is within the selected threshold distance, or optionally, within the selected threshold range. If yes, the process moves to block 414, where there is not an indication of not to ablate, and the indictors 112a and 112b are not illuminated. Optionally, the ablation catheter, if previously inactivated, is now activated, to perform the ablation, and the ablation spot is made.

If no at block 412, the "determined distance" or trajectory is either above or below (i.e., within) the selected threshold distance, or optionally, the selected threshold range. The process moves to block 416. At block 416, there is an indication at the indicator 112a on the panel 112, e.g., illumination of the light, or a red light, indicating that the determined distance or trajectory is above the threshold distance or optionally, the threshold range. Accordingly, the projected ablation spot based on the instant location of the electrode 26 of the ablation catheter 14, should not be made. This is because, for example, the resultant ablation spot made by the ablation catheter 14 will be separated from the previous ablation spot by a gap, which is highly undesired and dangerous.

Also, at block 416, there is an indication at the indicator 112b on the panel 112, e.g., illumination of the light, or a blue light, indicating that the determined distance or trajectory is below the threshold distance or optionally, the threshold range. Accordingly, the projected ablation spot based on the instant location of the electrode 26 of the ablation catheter 14, should not be made. This is because, for example, the resultant ablation spot made by the ablation catheter 14 will overlap with the previous ablation spot, potentially causing tissue overheating, a highly undesired and dangerous result.

Optionally, at block 416, an alert (visual audio or the like) may be issued from the system 300, to the physician or a device associated with the physician, not to ablate at this ablation catheter 14 location. Also optionally, the ablation catheter 14 may be deactivated, to be unable to make any ablations, until brought within a threshold distance of the previous ablation point.

From each of blocks 414 and 416, depending on the route of the process, the process moves to block 418. At block 418, should the ablation catheter 14 have moved its location within a predetermined time period, the process returns to block 404, from where it resumes by recalculating the "determined distance" or trajectory and applying a suitable threshold distance, and analyzing the "determined distance" with respect to the threshold distance, or optionally, the threshold range, to determine whether it is safe for the ablation catheter 14 to ablate at the projected ablation point. For example, the projected ablation point may be the projected next consecutive ablation point from the most recently ablated ablation point (previous ablation point), in the tissue 104.

If no at block 418, the ablation catheter 14/110 has not moved to a new location within the predetermined time period. The process moves to block 420 where it ends. The process can be resumed after it has ended at block 420.

Although the examples described herein mainly address ablation of cardiac tissue, other tissues may also be ablated by the apparatus and methods disclosed herein.

Although the examples disclosed herein refer mainly to usage of the disclosed techniques and systems during the ablation procedure, the disclosed techniques, systems and/or portions thereof can also be used in a planning phase before the ablation (ablation process) is performed, and/or after the ablation (ablation process) is performed.

EXAMPLES

Example 1

A method for ablating tissue comprising: determining a first ablation point in a tissue and an ablation mode associated with the first ablation point; determining a second ablation point in the tissue and the ablation mode associated with the second ablation point; selecting a threshold distance from one or more threshold distances, each of the one or more threshold distances corresponding to: 1) the ablation mode associated with the first ablation point and, 2) the ablation mode associated with the second ablation point; and, determining whether a distance between the first ablation point and the second ablation point is within the selected threshold distance.

Example 2

The method of Example 1, wherein the ablation mode comprises a plurality of ablation modes.

Example 3

The method of Example 1 or Example 2, wherein the plurality of ablation modes include Radio Frequency (RF) ablation and Pulsed Field Ablation (PFA).

Example 4

The method of any of Example 1 to Example 3, wherein if the distance between the first and second ablation points is within the threshold distance, allowing for ablation of the next consecutive ablation site.

Example 5

The method of any of Example 1 to Example 4, wherein if the distance between the first and second ablation points is not within the threshold distance, indicating that ablation should not proceed.

Example 6

The method of any of Example 1 to Example 5, wherein if the distance between the first and second ablation points is not within the threshold distance, adjusting the second ablation point to be within the threshold distance.

Example 7

The method of any of Example 1 to Example 6, wherein the second ablation point is the next consecutive ablation point after the first ablation point.

Example 8

The method of any of Example 1 to Example 7, wherein the first ablation point is represented by a tag (102, 103) on a map (100), and the second ablation point is provided as a location on the map (100).

Example 9

The method of any of Example 1 to Example 8, wherein the distance between the first ablation point on the map (100) and the second ablation point on the map (100) is measured on the map by a software-implemented caliper tool (310).

Example 10

The method of any of Example 1 to Example 9, wherein the software-implemented caliper tool (310) is adjusted to within the threshold distance when the previous distance between the first ablation point and the second ablation point exceeds the threshold distance.

Example 11

The method of any of Example 1 to Example 10, wherein the selecting a threshold distance from one or more threshold distances is performed automatically.

Example 12

The method of any of Example 1 to Example 11, wherein the one or more threshold distances are stored in storage media.

Example 13

The method of any of Example 1 to Example 12, wherein the one or more threshold distances include: 1) a first threshold distance between the first and second ablation points associated with RF ablation, 2) a second threshold distance between the first and second ablation points associated with PFA ablation, and 3) a third threshold distance between and the first and second ablation points, where one of the first or second ablation points is associated with RF ablation, and the other of the first or second ablation points is associated with PFA ablation.

Example 14

The method of any of Example 1 to Example 13, wherein the threshold distance comprises a range between: 1) a first distance based on potential overlap between the an ablation spot associated with the first ablation point and a projected ablation spot associated with the second ablation point, and 2) a second distance, greater than the first distance, the second distance based on the possibility of a gap between the ablation spot associated with the first ablation point and a projected ablation spot associated with the second ablation point.

Example 15

A system for ablating tissue comprising: an ablation catheter (14) for ablating tissue; a sensing catheter for sensing Intracardiac Electrogram (IEGM) signals in an area of tissue; a measuring tool (310); a mapping system in communication with the ablation catheter (14), the sensing catheter and the measuring tool, for creating an electronic map (100) from at least the IEGM signals; and, a processor (302) in communication with the mapping system, the processor (302) programmed to: determine 1) a first ablation point in the tissue and an ablation mode associated with the first ablation point; and, 2) a second ablation point in the tissue and the ablation mode associated with the second ablation point to be formed by the ablation catheter (14); select a threshold distance corresponding to: 1) the ablation mode associated with the first ablation point, and 2) the ablation mode associated with the ablation catheter (14) for the second ablation point; and, determine whether a distance between the first ablation point and the second ablation point, determined by the measuring tool (310) on the electronic map (100), is within the threshold distance.

Example 16

The system of Example 15, wherein the processor (302) is additionally programmed to signal an indicator (112*a*, 112*b*) when the distance between the first ablation point and the second ablation point is above or below the threshold distance.

Example 17

The system of Example 15 or Example 16, wherein the electronic map (100) is presentable on a display (27), and additionally comprising: an indicator panel (112) presentable on the display (27) comprising: 1) a first visible indicator (112*a*) for indicating that the distance between the first ablation point and the second ablation point is above the threshold distance, and 2) a second visible indicator (112*b*) for indicating that the distance between the first ablation point and the second ablation point is below the threshold distance.

Example 18

The system of any of Example 15 to Example 17, wherein the ablation catheter (14) and the sensing catheter are on the same catheter or are on different catheters.

Example 19

The system of any of Example 15 to Example 18, wherein the measuring tool (310) includes a caliper tool (310).

The implementation of the method and/or system of examples of the disclosure can involve performing or completing selected tasks manually, automatically, or a combination thereof. Moreover, according to actual instrumentation and equipment of examples of the method and/or system of the disclosure, several selected tasks could be implemented by hardware, by software or by firmware or by a combination thereof using an operating system or a cloud-based platform.

For example, hardware for performing selected tasks according to examples of the disclosure could be implemented as a chip or a circuit. As software, selected tasks according to examples of the disclosure could be implemented as a plurality of software instructions being executed by a computer using any suitable operating system. In an exemplary example of the disclosure, one or more tasks according to exemplary examples of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed examples of the present disclosure. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various examples of computer-implemented methods are provided herein, some of which can be performed by various examples of apparatuses and systems described herein and some of which can be performed according to instructions stored in non-transitory computer-readable storage media described herein. Still, some examples of computer-implemented methods provided herein can be performed by other apparatuses or systems and can be performed according to instructions stored in computer-readable storage media other than that described herein, as will become apparent to those having skill in the art with reference to the examples described herein. Any reference to systems and computer-readable storage media with respect to the following computer-implemented methods is provided for explanatory purposes and is not intended to limit any of such systems and any of such non-transitory computer-readable storage media with regard to examples of computer-implemented methods described above. Likewise, any reference to the following computer-implemented methods with respect to systems and computer-readable storage media is provided for explanatory purposes and is not intended to limit any of such computer-implemented methods disclosed herein.

The flowchart and block diagrams in the Figures illustrate the architecture, functionality, and operation of possible implementations of systems, methods, and computer program products according to various examples of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The descriptions of the various examples of the present disclosure have been presented for purposes of illustration but are not intended to be exhaustive or limited to the examples disclosed. Many modifications and variations will be apparent to those of ordinary skill in the art without departing from the scope and spirit of the described examples.

As used herein, the singular form "a", "an" and "the" include plural references unless the context clearly dictates otherwise.

It is appreciated that certain features of the disclosure, which are, for clarity, described in the context of separate examples, may also be provided in combination in a single example. Conversely, various features of the disclosure, which are, for brevity, described in the context of a single example, may also be provided separately or in any suitable sub-combination or as suitable in any other described example of the disclosure. Certain features described in the context of various examples are not to be considered essential features of those examples unless the example is inoperative without those elements.

The above-described processes including portions thereof can be performed by software, hardware, and combinations thereof. These processes and portions thereof can be performed by computers, computer-type devices, workstations, cloud-based platforms, processors, microprocessors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these examples to practice undue experimentation. The processes (methods) and systems have been described in a manner sufficient to enable persons of ordinary skill in the art to readily adapt other hardware and software as may be needed to reduce any of the examples to practice without undue experimentation and using conventional techniques.

Descriptions of examples of the disclosure in the present application are provided by way of example and are not intended to limit the scope of the disclosure. The described examples comprise different features, not all of which are required in all examples of the disclosure. Some examples utilize only some of the features or possible combinations of the features. Variations of examples of the disclosure that are described, and examples of the disclosure comprising different combinations of features noted in the described examples, will occur to persons of the art. The scope of the disclosure is limited only by the claims.

It will thus be appreciated that the examples described above, do not limit the disclosed subject matter to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for monitoring tissue ablation, the method comprising:

tracking a location of a distal end of a catheter within a heart chamber, the distal end comprising at least one electrode configured to deliver an ablation signal to cardiac tissue, wherein the ablation signal is generated by a generator electrically connected to the at least one electrode and configured to selectively generate the ablation signal using one of two distinct ablation modalities;

rendering on a display device a model of the heart chamber and a virtual representation of the distal end;

updating the rendering of virtual representation based on a current location of the distal end;

identifying a currently selected ablation modality, the current ablation modality being selected from the two distinct ablation modalities;

determining a distance between a projection of the current location on the cardiac tissue and a previous location at which an ablation signal was delivered;

identifying a previous ablation modality used at the previous location, wherein the previous ablation modality was selected from the two distinct ablation modalities, wherein the previous ablation modality is stored in memory associated with the display;

selecting a threshold distance from a plurality of predefined threshold distances based on the currently selected ablation modality and the previous ablation modality; and providing a first indication on the display device when the distance between the projection and a previous location is below the selected threshold distance.

2. The method of claim 1, wherein the two distinct ablation modalities include Radio Frequency (RF) ablation and Pulsed Field Ablation (PFA).

3. The method of claim 1, further comprising providing a second indication on the display device distinct from the first indication when the distance between the previous location and the projection is above the threshold distance.

4. The method of claim 1, wherein the projection is configured to be a next consecutive ablation location in an array of locations.

5. The method of claim 1, rendering a first tag on the map at the previous location, wherein the first tag has at least one of a size, color and pattern that indicates the ablation modality used at the previous location.

6. The method of claim 1, wherein the model is defined in three dimensions and wherein the distance between the previous location and the projection is measured in three dimensional space.

7. The method of claim 1, wherein the selecting the threshold distance from one or more predefined threshold distances is performed automatically.

8. The method of claim 1, wherein the plurality of predefined threshold distances include: 1) a first threshold distance defined for when both the previous ablation modality and the current ablation modality is RF ablation, 2) a second threshold distance defined for when both the previous ablation modality and the current ablation modality is PFA ablation, and 3) a third threshold distance for when one of the previous ablation modality and the current ablation modality is RF ablation, and the other of the previous ablation modality and the current ablation modality is PFA ablation.

9. The method of claim 1, wherein the threshold distance comprises a range between: 1) a first distance based on potential overlap between the previous ablation location and a current location, and 2) a second distance, greater than the first distance, the second distance based on the possibility of a gap between the previously ablation location and a current ablation location.

10. A system for monitoring tissue ablation, comprising:

a catheter including at least one distal electrode configured to deliver an ablation signal to cardiac tissue within a heart chamber, the electrode being electrically connected to a generator;

the generator configured to generate an ablation signal in two distinct ablation modalities;

a tracking system configured to track location of a distal end of the catheter, a processor programmed to:

generate a model of the heart chamber using locations tracked by the tracking system;

identify a currently selected ablation modality from the two distinct ablation modalities;

determine a distance between a projection of the current location on the cardiac tissue and a previous location where an ablation signal was delivered;

retrieve an ablation modality used at the previous location; and select a threshold distance from a plurality of predefined threshold distances, the selection based on the combination of the current and previous ablation modalities;

a display device configured to:

display a virtual representation of the catheter's distal end within the model of the heart chamber;

update the virtual representation in real time as the distal end moves; and provide a first visible indication on the display when the distance between the projection and the previous location is below the selected threshold distance.

11. The system of claim 10, wherein the processor is additionally programmed to provide a second visible indication on the display device that is distinct from the first indication when the distance between the projection and the previous location is below the selected threshold distance.

12. The system of claim 10, wherein the two distinct ablation modalities include Radio Frequency (RF) ablation and Pulsed Field Ablation (PFA).

* * * * *